(12) United States Patent  
Moalem

(10) Patent No.: US 9,393,087 B2  
(45) Date of Patent: Jul. 19, 2016

(54) METHODS AND SYSTEMS FOR GENERATING COLOR IMAGES

(71) Applicant: ALIGN TECHNOLOGY, INC., San Jose, CA (US)

(72) Inventor: Yosi Moalem, Ness-Ziona (IL)

(73) Assignee: ALIGN TECHNOLOGY, INC., San Jose, CA (US)

( * ) Notice: Subject to any disclaimer, the term of this patent is extended or adjusted under 35 U.S.C. 154(b) by 441 days.

(21) Appl. No.: 13/957,326

(22) Filed: Aug. 1, 2013

(65) Prior Publication Data

US 2015/0037750 A1 Feb. 5, 2015

(51) Int. Cl.
| | |
|---|---|
| *H04N 1/46* | (2006.01) |
| *G01B 11/24* | (2006.01) |
| *A61C 9/00* | (2006.01) |
| *A61B 5/00* | (2006.01) |
| *A61C 1/08* | (2006.01) |
| *A61B 5/107* | (2006.01) |
| *G02B 7/36* | (2006.01) |
| *H04N 5/232* | (2006.01) |
| *H04N 5/225* | (2006.01) |
| *H04N 9/04* | (2006.01) |

(Continued)

(52) U.S. Cl.
CPC ............ *A61C 9/0066* (2013.01); *A61B 5/0068* (2013.01); *A61B 5/0088* (2013.01); *A61B 5/1077* (2013.01); *A61C 1/088* (2013.01); *G01B 11/24* (2013.01); *G02B 7/36* (2013.01); *H04N 5/2256* (2013.01); *H04N 5/23212* (2013.01); *H04N 9/045* (2013.01)

(58) Field of Classification Search
CPC ................. A61C 19/004; A61C 1/088; A61N 2005/0652; A61B 1/06; A61B 1/24; A61B 1/00009; A61B 1/0638; A61B 1/0646; A61B 1/0005; A61B 1/043; A61B 1/00186; A61B 5/0071; A61B 5/0077; A61B 5/0084; A61B 6/466; A61B 1/04; A61B 1/045; A61B 1/063; A61B 5/0068; A61B 5/00; H04N 13/0271; H04N 9/045; H04N 9/735; H04N 13/0207; H04N 13/0257; H04N 5/2254; H04N 5/332; H04N 5/3696; H04N 13/021; H04N 13/0239; H04N 13/025; H04N 1/193; H04N 1/484; H04N 1/60; H04N 1/06
See application file for complete search history.

(56) References Cited

U.S. PATENT DOCUMENTS

| | | | |
|---|---|---|---|
| 2,467,432 | A | 4/1949 | Kesling |
| 3,407,500 | A | 10/1968 | Kesling |
| 3,600,808 | A | 8/1971 | Reeve |

(Continued)

FOREIGN PATENT DOCUMENTS

| | | | |
|---|---|---|---|
| AU | 3031677 | A | 5/1979 |
| AU | 517102 | B2 | 7/1981 |

(Continued)

OTHER PUBLICATIONS

AADR. American Association for Dental Research, Summary of Activities, Mar. 20-23, 1980, Los Angeles, CA, p. 195.

(Continued)

*Primary Examiner* — Sath V Perungavoor  
*Assistant Examiner* — Howard D Brown, Jr.  
(74) *Attorney, Agent, or Firm* — Wilson Sonsini Goodrich & Rosati

(57) ABSTRACT

Systems for generating in-focus color images are provided. Related methods and devices are also provided.

33 Claims, 11 Drawing Sheets

(51) Int. Cl.
 *H04N 13/02* (2006.01)
 *A61B 1/06* (2006.01)

(56) References Cited

U.S. PATENT DOCUMENTS

| | | | |
|---|---|---|---|
| 3,660,900 A | 5/1972 | Andrews |
| 3,683,502 A | 8/1972 | Wallshein |
| 3,738,005 A | 6/1973 | Cohen |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,971,065 A | 7/1976 | Bayer |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordon et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,402,707 B1 | 6/2002 | Ernst |
| 6,482,298 B1 | 11/2002 | Bhatnagar |
| 6,524,101 B1 | 2/2003 | Phan et al. |
| 6,554,611 B2 | 4/2003 | Chishti et al. |
| 6,572,372 B1 | 6/2003 | Phan et al. |
| 6,629,840 B2 | 10/2003 | Chishti et al. |
| 6,705,863 B2 | 3/2004 | Phan et al. |
| 6,722,880 B2 | 4/2004 | Chishti et al. |

(56) References Cited

U.S. PATENT DOCUMENTS

| | | | |
|---|---|---|---|
| 2002/0006597 A1 | 1/2002 | Andreiko et al. | |
| 2003/0009252 A1 | 1/2003 | Pavlovskaia et al. | |
| 2003/0139834 A1 | 7/2003 | Nikolskiy et al. | |
| 2003/0224311 A1 | 12/2003 | Cronauer | |
| 2004/0128010 A1 | 7/2004 | Pavlovskaia et al. | |
| 2005/0055118 A1 | 3/2005 | Nikolskiy et al. | |
| 2006/0001922 A1* | 1/2006 | Gawlik | H04N 1/484 358/505 |
| 2006/0060653 A1* | 3/2006 | Wittenberg | G06K 7/10732 235/462.01 |
| 2010/0270376 A1* | 10/2010 | McQueen | G06K 7/10722 235/462.11 |
| 2011/0043661 A1* | 2/2011 | Podoleanu | A61B 3/102 348/239 |
| 2011/0085219 A1* | 4/2011 | Yang | G02B 5/32 359/15 |
| 2012/0075425 A1 | 3/2012 | Thiel | |
| 2012/0092678 A1* | 4/2012 | Babayoff | A61B 1/00009 356/601 |
| 2014/0015932 A1* | 1/2014 | Kim | H04N 13/0257 348/46 |

FOREIGN PATENT DOCUMENTS

| | | |
|---|---|---|
| AU | 5598894 A | 6/1994 |
| CA | 1121955 | 4/1982 |
| DE | 2749802 | 5/1978 |
| DE | 69327661 T | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 8/1995 |
| EP | 0731673 B1 | 9/1996 |
| EP | 0774933 B1 | 5/1997 |
| EP | 1610166 A1 | 12/2005 |
| ES | 463897 | 1/1980 |
| FR | 2369828 A1 | 6/1978 |
| FR | 2652256 A1 | 3/1991 |
| GB | 15500777 | 8/1979 |
| JP | 53-058191 | 5/1978 |
| JP | 04-028359 | 1/1992 |
| JP | 08-508174 | 9/1996 |
| JP | 4885439 B2 | 2/2012 |
| WO | WO 90/08512 A1 | 8/1990 |
| WO | WO 91/04713 A1 | 4/1991 |
| WO | WO 94/10935 A1 | 5/1994 |
| WO | WO 98/32394 A1 | 7/1998 |
| WO | WO 98/44865 A1 | 10/1998 |
| WO | WO 98/58596 A1 | 12/1998 |
| WO | WO 2010/145669 A1 | 12/2010 |

OTHER PUBLICATIONS

Alcaniz, et al. "An Advanced System for the Simulation and Planning of Orthodontic Treatments," Karl HF Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.
Alexander et al., "The DigiGraph Work Station Part 2 Clinical Management," JCO, pp. 402-407 (Jul. 1990).
Altschuler et al., "Analysis of 3-D Data for Comparative 3-D Serial Growth Pattern Studies of Oral-Facial Structures," AADR Abstracts, Program and Abstracts of Papers, 57th General Session, IADR HP Annual Session, Mar. 29, 1979-Apr. 1, 1979, New Orleans Marriot, Journal of Dental Research, vol. 58, Jan. 1979, Special Issue A, p. 221.
Altschuler et al., "Laser Electro-Optic System for Rapid Three-Dimensional (3D) Topographic Mapping of Surfaces," Optical Engineering, 20(6):953-961 (1981).
Altschuler et al., "Measuring Surfaces Space-Coded by a Laser-Projected Dot Matrix," SPIE Imaging Applications for Automated Industrial Inspection and Assembly, vol. 182, p. 187-191 (1979).
Altschuler, "3D Mapping of Maxillo-Facial Prosthesis," AADR Abstract #607, 2 pages total, (1980).
Andersson et al., "Clinical Results with Titanium Crowns Fabricated with Machine Duplication and Spark Erosion," Acta. Odontol. Scand., 47:279-286 (1989).
Andrews, The Six Keys to Optimal Occlusion Straight Wire, Chapter 3, pp. 13-24 (1989).
Bartels, et al., An Introduction to Splines for Use in Computer Graphics and Geometric Modeling, Morgan Kaufmann Publishers, pp. 422-425 (1987).
Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.
Baumrind et al., "Mapping the Skull in 3-D," reprinted from J. Calif. Dent. Assoc., 48(2), 11 pages total, (1972 Fall Issue).
Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.
Baumrind, "Integrated Three-Dimensional Craniofacial Mapping: Background, Principles, and Perspectives," Semin. in Orthod., 7(4):223-232 (Dec. 2001).
Begole et al., "A Computer System for the Analysis of Dental Casts," The Angle Orthod., 51(3):253-259 (Jul. 1981).
Bernard et al.,"Computerized Diagnosis in Orthodontics for Epidemiological Studies: A ProgressReport," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff et al., "Computerized Analysis of Occlusion in the Postcanine Dentition," Am. J. Orthod., 61(3): 245-254 (Mar. 1972).
Biggerstaff, "Computerized Diagnostic Setups and Simulations," Angle Orthod., 40(1):28-36 (Jan. 1970).
Biostar Opeation & Training Manual. Great Lakes Orthodontics, Ltd. 199 Fire Tower Drive,Tonawanda, New York. 14150-5890, 20 pages total (1990).
Blu, et al., "Linear interpolation revitalized", IEEE Trans. Image Proc., 13(5):710-719 (May 2004).
Bourke, "Coordinate System Transformation," (Jun. 1996), p. 1, retrieved from the Internet Nov. 5, 2004, URL <http://astronomy.swin.edu.au/-pbourke/prolection/coords>.
Boyd et al., "Three Dimensional Diagnosis and Orthodontic Treatment of Complex Malocclusions With the Invisalipn Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone (interview), "Dr. Charles J. Burstone on The Uses of the Computer in Orthodontic Practice (Part 1)," J. Clin. Orthod., 13(7):442-453 (Jul. 1979).
Burstone (interview), "Dr. Charles J. Burstone on The Uses of the Computer in Orthodontic Practice (Part 2)," J. Clin. Orthod., 13(8):539-551 (Aug. 1979).
Burstone et al., Precision Adjustment of the Transpalatal Lingual Arch: Computer Arch Form Predetermination, Am, Journal of Orthodontics, vol. 79, No. 2 (Feb. 1981), pp. 115-133.
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).

(56) References Cited

OTHER PUBLICATIONS

Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1: CAD/CAM: The Computer Moves Chairside," "Part 2: F. Duret—A Man With a Vision," "Part 3: The Computer Gives New Vision—Literally," "Part 4: Bytes 'N Bites" The Computer Moves From the Front Desk to The Operatory, Canadian Dental Journal, vol. 54(9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin Orthod., 7(4):258-265 (Dec. 2001).
Cutting et al., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production, pp. 1-7 (Jan. 1992).
Definition for gingiva. Dictionary.com p. 1-3. Retrieved from the internet Nov. 5, 2004 <http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium on Computer Restorations: State of the Art of the CEREC-Method, May 1991, 2 pages total.
Dentrac Corporation, Dentrac document, pp. 4-13 (1992).
Dent-X posted on Sep. 24, 1998 at <http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances-Pro Lab, 1 page (1997).
Duret et al, "CAD-CAM in Dentistry," J. Am. Dent. Assoc. 117:715-720 (Nov. 1988).
Duret et al., "CAD/CAM Imaging in Dentistry," Curr. Opin. Dent., 1:150-154 (1991).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Faber et al., "Computerized Interactive Orthodontic Treatment Planning," Am. J. Orthod., 73(1):36-46 (Jan. 1978).
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et al., "Automated Finite Element Modeling of a Human Mandible with Dental Implants," JS WSCG '98—Conference Program, retrieved from the Internet: <http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982).
Grayson, "New Methods for Three Dimensional Analysis of Craniofacial Deformity, Symposium: Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989).
Heaven et al., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingamp-production/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances—Pro Lab, 1 page 1998).
JCO Interviews, Craig Andreiko , DDS, MS on the Elan and Orthos Systems, JCO, pp. 459-468 (Aug. 1994).
JCO Interviews, Dr. Homer W Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling et al., The Philosophy of the Tooth Positioning Appliance, American Journal of Orthodontics and Oral surgery. 1945; 31:297-304.
Kesling, Coordinating the Predetermined Pattern and Tooth Positioner with Conventional Treatment, Am. J. Orthod. Oral Surg. (1946) 32:285-293.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.

(56) References Cited

OTHER PUBLICATIONS

Laurendeau, et al., "A Computer-Vision Technique for the Acquisition and Processing of 3-D Profiles of 7 Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy as One, Two, Three," AOA/Pro Corner, vol. 11, No. 1, 2 pages (2002).
Mormann et al., "Marginale Adaptation von adhasuven Porzellaninlays in vitro," Separatdruck aus:Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
PROCERA Research Projects, "PROCERA Research Projects 1993—Abstract Collection," pp. 3-7, 28 (1993).
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine Table of contents and Essix Appliances, <http://www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording The Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Surg., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively).
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice is Clear: Red, White & Blue . . . The Simple, Affordable, No-Braces Treatment, Allesee Orthodontic Appliances—Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee Orthodontic Appliances—Pro Lab product information for patients, <http://ormco.com/aoa/appliancesservices/RWB/patients.html>, 2 pages (May 19, 2003).
The Choice is Clear: Red, White & Blue . . . The Simple, Affordable, No-Braces Treatment, Allesee Orthodontic Appliances—Pro Lab product information, 6 pages (2003).
The Red, White & Blue Way to Improve Your Smile! Allesee Orthodontic Appliances—Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden et al., "Three-Dimensional Analysis of Dental Casts by Means of the Optocom," J. Dent. Res., p. 1100 (Jul.-Aug. 1972).
Van Der Linden, "A New Method to Determine Tooth Positions and Dental Arch Dimensions," J. Dent. Res., 51(4):1104 (Jul.-Aug. 1972).
Van Der Zel, "Ceramic-Fused-to-Metal Restorations with a New CAD/CAM System," Quintessence Int., 24(11):769-778 (1993).
Varady et al., "Reverse Engineering of Geometric Models—An Introduction," Computer-Aided Design, 29(4):255-268,1997.

(56) References Cited

OTHER PUBLICATIONS

Verstreken et al., "An Image-Guided Planning System for Endosseous Oral Implants," IEEE Trans. Med. Imaging, 17(5):842-852 (Oct. 1998).

Warunek et al., Physical and Mechanical Properties of Elastomers in Orthodonic Positioners, Am J. Orthod. Dentofac. Orthop, vol. 95, No. 5, (May 1989) pp. 399-400.

Warunek et.al., Clinical Use of Silicone Elastomer Applicances, JCO (1989) XXIII(10):694-700.

Wells, Application of the Positioner Appliance in Orthodontic Treatment, Am. J. Orthodont. (1970) 58:351-366.

Williams, "Dentistry and CAD/CAM: Another French Revolution," J. Dent. Practice Admin., pp. 2-5 (Jan./Mar. 1987).

Williams, "The Switzerland and Minnesota Developments in CAD/CAM," J. Dent. Practice Admin., pp. 50-55 (Apr./Jun. 1987).

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.

WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.

Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).

Yamamoto et al., "Optical Measurement of Dental Cast Profile and Application to Analysis of Three-Dimensional Tooth Movement in Orthodontics," Front. Med. Biol. Eng., 1(2):119-130 (1988).

Yamamoto et al., "Three-Dimensional Measurement of Dental Cast Profiles and Its Applications to Orthodontics," Conf. Proc. IEEE Eng. Med. Biol. Soc., 12(5):2051-2053 (1990).

Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.

Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).

Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).

Yoshii, "Research on a New Orthodontic Appliance: The Dynamic Positioner (D.P.); Ill.—The General Concept of the D.P. Method and Its Therapeutic Effect, Part 2. Skeletal Reversed Occlusion Case Reports," Nippon Dental Review, 458:112-129 (Dec. 1980).

Yoshii, "Research on a New Orthodontic Appliance: The Dynamic Positioner (D.P.); Ill. The General Concept of the D.P. Method and Its Therapeutic Effect, Part 1, Dental and Functional Reversed Occlusion Case Reports," Nippon Dental Review, 457:146-164 (Nov. 1980).

You May Be a Candidate for This Invisible No-Braces Treatment, Allesee Orthodontic Appliances—Pro Lab product information for patients, 2 pages (2002).

International preliminary report on patentability dated Feb. 2, 2016 for PCT/IB2014/001456.

International search report and written opinion dated Dec. 2, 2015 for PCT/IB2014/001456.

\* cited by examiner

METHODS AND SYSTEMS FOR GENERATING COLOR IMAGES

BACKGROUND

Various techniques can be used for obtaining the three dimensional (3D) topography of an object. Information regarding 3D topography of a surface can be used to image a plethora of objects and surfaces. For example, 3D topography data can be used for a host of applications including applications in dental imaging and restoration. In some instances, 3D imaging methodologies can be used for imaging an oral cavity of a patient. With the additional use of computer-assisted design (CAD) or computer-assisted manufacture (CAM) methods, tooth replacements can be designed and manufactured without having to make any cast impressions of a patient's teeth. Imaging systems can, e.g., include an optical probe coupled to a detector and a processor for generating a suitable image to allow for design and fabrication of a desired product (e.g., a physical model and/or prosthesis).

Associating color information with three-dimensional objects is not straightforward, particularly when the position information is obtained by using a three dimensional scanning method and the color information is obtained using a two dimensional scanning method. The problem of conformally mapping the two dimensional color information onto the three dimensional surface model is difficult and it is common for mismatching of the color with three-dimensional points to occur. For example, it can be difficult to accurately associate color information from the detectors with the correct points on the three dimensional surface model, particularly if relative movement between the object and the device occurs between the acquisition of the three-dimensional topological data and acquisition of the two-dimensional image data.

Thus, there is a need for improved methods and systems for generating color images, e.g., focused color images, of an object, such as a patient's dentition.

SUMMARY

Systems, methods, and devices for generating color images of an object are provided. For example, in many embodiments, the systems, methods, and devices generate focused two-dimensional (2D) color images of an object (e.g., a patient's dentition) in combination with three-dimensional (3D) topography data of the object. The multi-focal color image generation disclosed herein provides enhanced color acquisition relative to single focal color image generation. Additionally, the systems, methods, and devices disclosed herein can be used to concurrently acquire in-focus color images and corresponding 3D topography data.

In some aspects, methods are provided for generating a focused color image of an object. The methods can include illuminating the object with a light source, wherein a first wavelength of light and a second wavelength of light from the light source are focused in a first focal plane and a second focal plane. A detector can be used to collect first image data of the illuminated object at a first time point. The first image data can correspond to the first wavelength of light reflected from the object at the first focal plane. The same or a different detector can also be used to collect second image data of the illuminated object at a second time point. The second image data can correspond to the second wavelength of light reflected from the object at the second focal plane. The first and second image data can then be combined to generate the focused color image of the object. Related methods, systems and devices are also provided.

Other objects and features of the present invention will become apparent by a review of the specification, claims and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

A better understanding of the features and advantages of the present invention can be obtained by reference to the following detailed description that sets forth illustrative embodiments, in which the principles of the invention are utilized, and the accompanying drawings of which.

DETAILED DESCRIPTION

Figure 1:
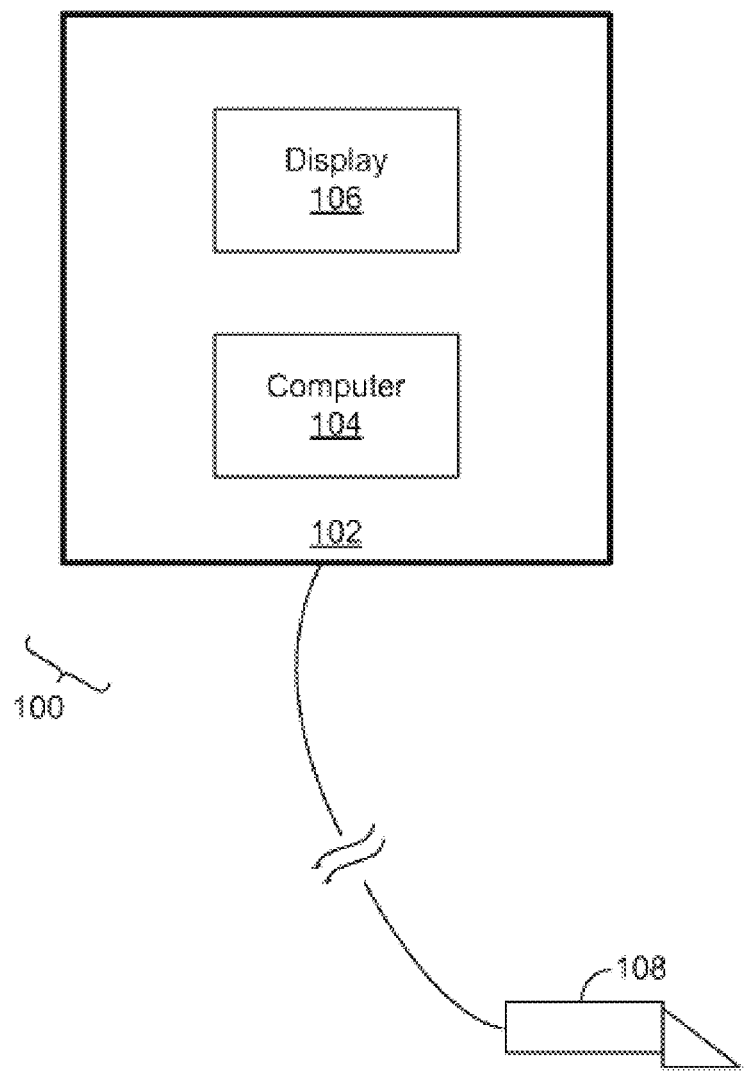
FIG. 1 depicts an example system for generating color and 3D topography images, in accordance with an embodiment.

Systems, methods and devices for generating color images of an object are provided. For example, in many embodiments, systems, methods, and/or devices generate focused two-dimensional (2D) color images of a patient's dentition in combination with three-dimensional (3D) topography data of the patient's dentition.

The methods and systems provide, among many features, fast and easy acquisition of color and 3D topography data representing an object. For example, the methods and systems can be used to collect 2D color images that are in focus and accurately represent an object. In addition, 3D topographical data of the surface of the object can be generated in real-time and in combination with the 2D color image data. In one aspect, the 3D topographical data and 2D color image data can be processed and combined together to be output to a display for user visualization. Based at least in-part on the methods and systems described herein, new and improved ways are provided to generate in-focus color images (e.g., RGB images) of an object that can overlaid with 3D image data corresponding to the object. In existing approaches, in which color imaging and 3D data acquisition are not both performed over a shared period of time, the combined total time required to separately acquire a color image and separately perform 3D topography scanning may be longer than desirable with respect to operator convenience and/or patient comfort. Additionally, when a hand held imaging scanner is employed, the acquisition of a color image and performance of 3D topography scanning is preferably performed at close to the same time so as to avoid possible detrimental movement of the scanner. In contrast to such existing approaches, the methods and systems disclosed herein can be used to acquire an color image and perform 3D topography scanning over a shared period of time, thereby reducing the total amount of time required and help avoid detrimental movement of the scanner as a result of the reduced total amount of time, as well as a result of the ability to obtain color image data and 3D topography data for portions of the object at substantially the same time.

Any suitable type of object can be imaged. In one embodiment, the scanning methods and systems can be used to generate images representing a patient's teeth. For example, some or all of a patient's teeth can be scanned and provided for display to a user. Using the 3D topographical data, for example, 3D virtual models of the patient's teeth can be displayed and manipulated, e.g., to facilitate a dental practitioner in a dental procedure. In some instances, e.g., the 3D virtual models can be used to define spatial relationships of a patient's teeth to define how to manufacture a dental prosthesis (e.g., a crown or a bridge) shaped to fit that particular patient's occlusion. In addition to displaying a 3D virtual model, the methods and systems described herein provide for display of color information of the patient's teeth. For example, gums and teeth can be easily distinguished by color and that color information can also be combined with the 3D topographical data to produce focused color images that can be combined with the 3D topographical data to produce color 3D virtual models. The data generated by the systems and methods can also shared and stored to be later transmitted or output, e.g., to manufacturing devices that can be used to make physical models and/or physical replicas of a dental prosthesis that is designed virtually.

In one aspect, a system is provided for generating a focused color image of an object. The system can include a polychromatic light source that can be used, e.g., to produce light for generating color images. The polychromatic light can be reflected off a surface of an object and then imaged to produce color images. To facilitate production of color images, the system can include an optics system optically coupled to the light source so as to focus the polychromatic light at a first focal plane and a second focal plane, in which the first focal plane includes one color (e.g., red) and the second focal plane includes another color (e.g., green). In some embodiments, a third color (e.g., blue) can be focused at a third focal plane. The focal planes of the different colors of light can be scanned over the surface of an object and the different colors of light can be reflected to allow for collection of color image data representing the surface of the object. In some aspects, the system can include a detector configured to collect color image data at different time points in a scanning procedure. For example, image data corresponding to one color (e.g., red) of the polychromatic light source can be collected at a first time point. Image data for another color (e.g., green) can be collected at a second time point. Due in part to the different Z-locations of focal points for the red and green colors, the green color image data can be in focus while the red color image data will not be in focus. As the focal planes are scanned during the scanning procedure, the red focus can be moved such that red image data is in focus and the green is not in focus. The collected image data of the focused red and green images can then be processed by a processor configured to combine the color image data to generate the focused color image of the object.

In some embodiments, focused color images can be produced, e.g., by collecting in-focus image data of the color data for each color of the polychromatic light at different time points in which each color is independently in focus. Given that the different colors can be in different focal planes, one color may be in focus while another color is not in focus because the object will be in the vicinity of one color's focal plane but not the other. Depending on the position of the different colors of light in relation to an object (e.g., the focal planes for each different color), focused image data for one color (e.g., red) can be generated and collected from the object. At that time point of collection for the one color, another color (e.g., blue) may not produce in-focus color data. Instead, focused image data for the other color (e.g., blue) can be collected at a different time point in a scan of the object, such that the other color is in focus and the one color (e.g., red) is not in focus. The focused color image data at each time point can then be combined to produce an in-focus red and blue image. Other color combinations can also be used to generate, e.g., real RGB images of an object.

A variety of imaging systems can be used to produce the in-focus color images as described herein. An imaging system that produces different colors at different focal planes can be used. The different focal planes associated with the different colors can be scanned over the surface of an object to generate reflections from the surface. The colored reflections can be collected and imaged using detectors and then processed to produce in-focus images. The processing can include selecting different color information at different time points, e.g., in which one color is in focus at one time point and another color is in focus at another time point. The in-focus image data for the one color can be combined with in-focus image data of the other color, thereby producing an in-focus image that includes color data for both colors. Similarly, this can be applied to multiple color configurations. For example, in-focus image data for red, green and blue images can be combined to form an in-focus RGB image.

In another aspect, a system is provided for generating images of a patient's teeth. The system includes a color detector including a two-dimensional pixel array that includes: (a) a plurality of first pixels distributed within the pixel array, (b) a plurality second pixels distributed within the pixel array, and (c) a plurality of third pixels distributed within the pixel array. Each of the first pixels is configured to detect a first wavelength of light reflected from the patient's teeth. Each of the second pixels is configured to detect a second wavelength of light reflected from the patient's teeth different from the first wavelength. Each of the third pixels is configured to detect a third wavelength of light reflected from the patient's teeth different from the first and second wavelengths. The system further includes a processor operatively coupled to the first pixels, the second pixels, and the third pixels.

The first, second, and third wavelengths of light can be any suitable combination of different wavelengths. For example, the first wavelength can correspond to red light, the second wavelength can correspond to green light, and the third wavelength can correspond to blue light.

In many embodiments of the system for generating images of a patient's teeth, the pixel array includes a repeating pattern of the first pixels, the second pixels, and the third pixels. For example, the repeated pattern can consist of two of the first pixels, one of the second pixels, and one of the third pixels arranged in a two by two array.

In many embodiments of the system for generating images of a patient's teeth, the processor is configured to process signals received from the first pixels, the second pixels, and the third pixels to generate: (a) first image data at a first time point, (b) second image data at a second time point different from the first time point, and (c) third image data at a third time point different from the first and second time points. The first image data is generated in response to signals from the first pixels. The second image data is generated in response to signals from the second pixels. The third image data is generated in response to signals from the third pixels. The processor is configured to combine the first image data, the second image data, and the third image data to generate a focused color image of the patient's teeth. The processor can also be configured to process signals from the first pixels, the second pixels, and the third pixels to generate surface topology data for the patient's teeth.

Referring to FIG. 1, a scanning system 100 can include a computer system 102 having a computer 104 and a display 106. The system 100 can also include a scanner 108 that can be used to scan an object, e.g., a patient's dentition. The scans can be used, e.g., to generate three dimensional (3D) digital models of an object. The computer system 100 can include a microprocessor, memory, or any other suitable hardware configured to process a scanned image of the patient and the device having the coded pattern. The computer system 100 can also include input modules such as a keyboard, mouse, and/or tablet. The display 106 (or output device) can include a screen or monitor but may also include a printer, or any other display system. The display of the system, e.g., can be used to show the generated 3D digital models of an object.

A variety of scanners can be used, e.g., to acquire scan images of an object, such as a patient's teeth. The scanner 108, for example, can be configured to acquire surface topology of structures, e.g., dental surfaces of dental structures and/or other tissue surfaces of the face and head of a patient. In one embodiment, the scanner 108 can be used to acquire scan image data for 3D digital models of at least a portion of the patient's teeth. As shown in FIG. 1, the scanner 108 is also operatively connected to the computer system 102. The computer system 102 can be programmed for reconstructing scanned surfaces from the surface data provided, to provide a corresponding digital model of the structure scanned by the scanner. The scanner 108 may also include, for example, any suitable non-contact scanner, for example an optical scanner.

In some embodiments, color image data of the intraoral cavity is acquired together with the scan image data to provide a digital model that includes 3D digital data representing the surfaces of the structures as well as color information of the structures scanned, such as for example of dental surfaces.

The scanning systems can also be used for generating color images and/or 3D digital models of all or a portion of an intraoral cavity. In some embodiments, the system can also be configured to scan and generate color images and/or 3D digital models of the upper and/or lower arch of the patient. In certain embodiments, the system can be configured to scan and generate color images and/or 3D digital models of the upper and lower arches together in occlusion. As described further herein, the color images and/or 3D digital models can be used for certain aspects of the methods described herein. For example, the color images and/or 3D digital models can be used in alignment procedures and/or for generating physical models that accurately represent actual positions of the patient's teeth when the models are mounted in an articulator. The color images and/or 3D digital models can include topographical data and/or color data representing a variety of dental structures such as one or more teeth, partial or the full mandibular or maxillary arches, or both arches, and/or details of the spatial relationship between the upper and lower arches in occlusion as well as surrounding tissue, such as gums, and other dental prosthetics (e.g., crowns).

The 3D digital models can be acquired using a variety of suitable methods. In one embodiment, 3D digital models can be obtained by scanning a patient's intraoral cavity using any suitable equipment for scanning a patient's teeth. Such scanning equipment may include any suitable optical scanner, for example, the scanner 108 of system 100, a similar scanner that is not part of the system 100, or a different type of scanner. In alternative embodiment, the 3D digital models can be obtained from a physical model of the teeth of the particular patient. For example, the surfaces of the physical model can be scanned, or the surfaces of the impression from which the model was scanned can be scanned to obtain the digital model. In some embodiments, scans can be taken of physical models of a patient's lower arch, upper arch, and the arches in occlusion. Together with a scan of the coded pattern at least a portion of the patient's teeth, the physical models can then be modified, e.g., with alignment structures that provide for accurate representation of the patient's occlusion when the models are mounted in an articulator (e.g. holes in the models can have predetermined shapes, sizes and/or orientations for accurate mounting in an articulator). In some embodiments, a composite positive-negative model can be manufactured and processed to obtain 3D digitized data. Alternatively, the 3D digitized data may be obtained in any other suitable manner, including other suitable intra oral scanning techniques, based on optical methods, direct contact methods or any other means, applied directly to the patient's dentition or to a physical model thereof. X-ray based, CT-based, MRI-based, or any other type of scanning of the patient or of a positive and/or negative physical model of the intra-oral cavity can be used, as well. 3D digital models can also be obtained by other ways, such as from an electronic record or another practitioner or scanning facility.

Figure 2:
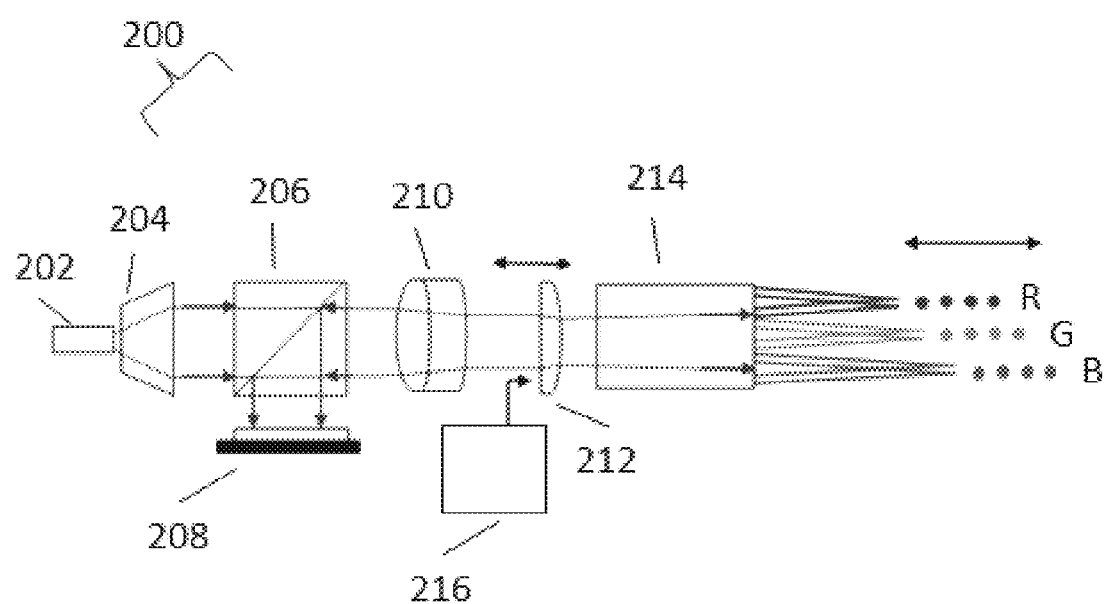
FIG. 2 illustrates an example device for collecting 3D and/or color image data, in accordance with an embodiment.

A variety of scanning confocal devices can be used and combined, e.g., with the methods of generating in-focus color images described further herein. Example scanning devices can be found, e.g., in U.S. Publication No. US2012/0092678 and WO 00/08415, each of which is incorporated by reference herein. Referring to FIG. 2, an imaging device 200 that can be used for generating 3D topography and color images of an object is illustrated. As shown, a light source 202 for generating a light beam that can be illuminated through a confocal system 204 configured to split the light beam into a plurality of light beams that can, e.g., be directed through the imaging device and illuminated onto an object, e.g., a surface of a patient's teeth. As shown, the light beams can be optically coupled to a splitting optic 206 that can be, e.g., a beamsplitter or other optic configured to pass the illuminating light beams and redirect light beams that are reflected from the surface of the object. In some embodiments, the splitting optic 206 can be a dichroic mirror. The arrows in the imaging device of FIG. 2 provide additional reference for this concept. The imaging device 200 can also include other optical components, e.g., a lens and/or a mirror that can be used to direct light in the device. For example, lens 210 can be a static lens positioned in the imaging device, e.g., so as to allow for focusing of the reflected light beams onto surface of a detector 208. Other optical components can also be used in the device. For example, a dynamic lens 212 can be positioned in the device to allow for scanning of the object through focal planes in space. For purposes of explanation only, and not to be limiting, the relative dimension of scanning can be along a Z-axis that is perpendicular to an X-Y plane. The X-Y plane can be an arbitrary reference plane that can be referenced in relation to the device and/or the object. The dynamic lens 212 can be used to change the focal plane of light from the imaging device in relation to, e.g., a surface of an object. As shown by the double arrows in FIG. 2, the dynamic lens 212 can be moved back and forth (short double arrow) in the device 200, thereby allowing for scanning of the light illuminated by the device as indicated by the longer double arrow in the vicinity of the focal planes of light generated by the imaging device 200. One of ordinary skill in the art will appreciate the myriad ways to scan light using an imaging device, as disclosed herein. For example, the dynamic lens can be coupled to a motor or other mechanism for moving the lens in the device. A liquid lens, the shape of which can be controllably changed to controllably change the focal length of the liquid lens, can also be used.

In some embodiments, the imaging device 200 can include a probe 214 that is used for scanning an object, as further described herein. The probe can be a handheld probe. In some aspects, the probe can be fully integrated along with other components of the imaging device 200, as shown, e.g., in FIG. 2. Other embodiments can include having the probe 214 separated from some or all of the other components in imaging device 200. For example, the probe 214 may be handheld unit optically coupled to a standing unit that includes, e.g., the light source 202, lenses 210 and 212, and the detector 208. In some embodiments, the detector 208 may be housed in a separate unit from the other optical components and/or the probe 214. The detector 208 can be a color or monochrome image sensor, e.g., a CMOS or CCD camera.

In many embodiments, a polychromatic light source 216 is coupled to the imaging device so as to allow for scanning the object with several colors of light. Virtually any suitable colors or wavelengths can be used. The polychromatic light source can be used to produce a light beam having at least two wavelengths (e.g., a first wavelength and a second wavelength of light). Any suitable wavelength of light can be used. A line wavelength of light, such as the light produced by a laser, can be used or broader ranges of wavelengths of light that have a max wavelength with a spread, such as light produced by a light emitting diode can also be used. The polychromatic light source generally can output wavelengths of light that can allow for collection and generation of color images that can be used to simulate the colors of an object. For example, the wavelengths of light used for imaging can be used to show color of a patient's reddish gums versus a patient's whitish teeth.

The polychromatic light source 216 can also be coupled (e.g., optically coupled) to the rest of the imaging device 200. For example, a white light source (e.g., a white LED) can be optically coupled into the dynamic lens 212 so as to allow for focusing of the R, G, and B focal planes in the vicinity or overlapped with the focal plane of the plurality of light beams produced using the light source 202 and the confocal system 204. In some embodiments, the polychromatic light source can include a plurality of different wavelength light sources (e.g., red, green and blue LEDs) that can be arranged in a ring structure around the dynamic lens 210. In some embodiments, the polychromatic light source can include a plurality of LEDs (e.g., white LEDs) that can be arranged in a ring configuration around the dynamic lens 210. The positions of the LEDs in the ring can be designed to orient the emitted light to be coincident with the confocal light beams illuminating the surface of an object. Furthermore, the polychromatic light source can further be integrated into the system to provide homogeneous illumination of the surface of an object using polychromatic light.

In some embodiments, the optics in the imaging device 200 and the coupling of the polychromatic light source 216 can be configured to produce different focal planes for different colors of light. For example, the focal planes can correspond to red (R), green (G) and blue (B) light that can be used to scan a surface of an object. As shown in FIG. 2, the focal planes for the red light, green light and blue light can be at different positions along an axis. For example, an X-Y plane having red light can be at one position of a Z-axis, an X-Y plane having green light can be at another position of the Z-axis, and an X-Y plane having blue light can be at another position of the Z-axis.

The relative positions of the different colors at different focal planes can be depend on a variety of factors, such as the color of the light, refractive indices of the optical components, and/or use of optics that amplify chromatic aberrations that can cause the different colors to be focused at different focal planes. In some aspects, the different focal planes depending on the color (or wavelength) of light can be generated using a variety of techniques. In one embodiment, chromatic aberration from lens or other optics can be used to produce different focal planes having different wavelengths of light. In an alternative embodiment, optical components can be provided for each wavelength and arranged to generate different focal planes for each color. FIG. 2 represents the R, G and B focal points as being separated in an X-Y plane. However, the different R, G and B focal points can be arranged along a Z-dimension that is perpendicular to the X-Y plane. It will also be generally understood by one of ordinary skill in the art that the R, G, and B focal points can represent planes of red, green and blue light generated by the imaging device 200. These planes of different colored light can be scanned over the surface of an object and reflected back into the imaging device 200 and imaged using the detector 208.

As described above, the systems can include components to produce both color image data and 3D topographical data either independently or together. The collection of the data can be carried out using a variety of methodologies. For example, the same or different detectors in the system can be used to collect 2D and/or 3D image data. As shown in FIG. 2, the same detector 208 can be used to collect reflected light from the polychromatic light source 216 and the monochromatic light from light source 202. As also described, a light beam from light source 202 can be split into a plurality of light beams that can be transferred optically through the imaging device 200. In some embodiments, the light beam can be split into an array of light beams that can then be focused in a focal plane that will include an array of focal spots corresponding to the array of light beams. This array can be used, e.g., for confocal scanning of an object and for imaging the surface of the object to obtain 3D topographical data representing the object's surface. In some embodiments, the array of light beams can be combined such that the light beams are spatially overlaid with light that is generated by the polychromatic light source.

Figure 3:
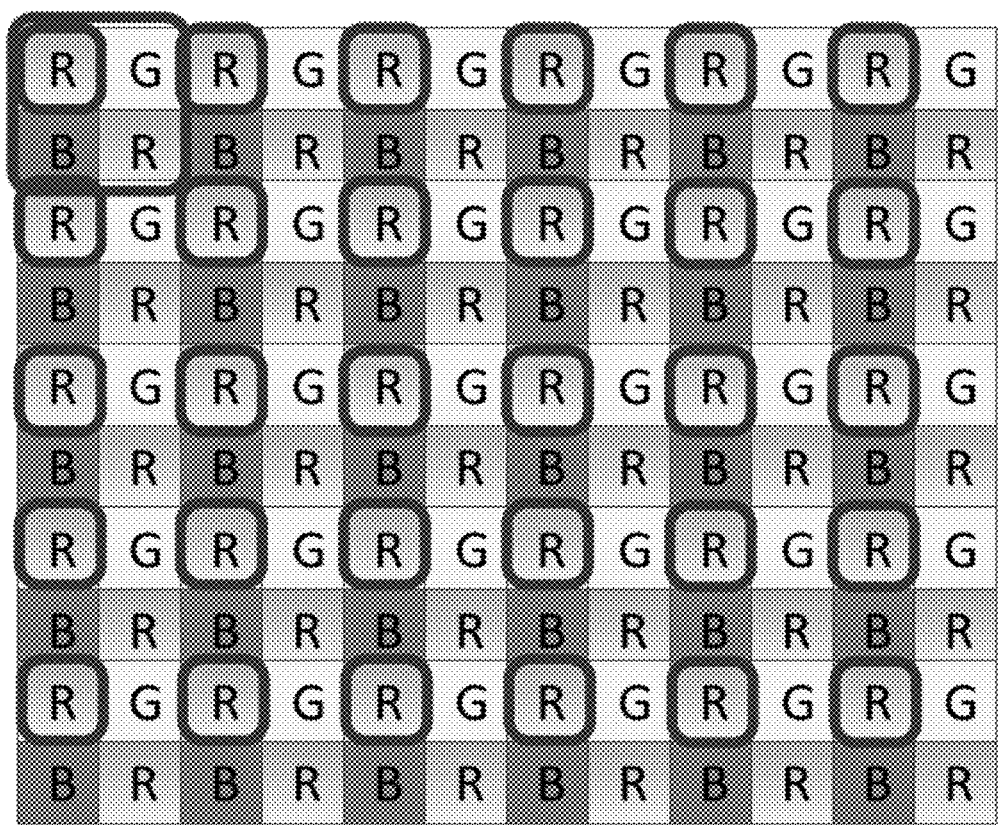
FIG. 3 illustrates an example pattern for color recognition by a color detector, in accordance with an embodiment.

In one embodiment, a color detector can be used to collect both the color image data associated with the polychromatic light source and the 3D topographical data associated with the monochromatic array of light beams. For example, the color detector (e.g., detector 208 in FIG. 2) can have a desired pixel pattern for collecting color and 3D topographical data. While any suitable pixel array pattern can be used, in a preferred embodiment, the pixel array pattern has a red majority pixel arrangement, for example, as illustrated in FIG. 3. The arrangement illustrated in FIG. 3 is a preferred arrangement when a corresponding red wavelength is used as a monochrome topography capture wavelength. In a similar fashion, a blue majority arrangement, where the blue and the red color pixels change position in FIG. 3, is a preferred arrangement when a corresponding blue wavelength is used as a monochrome topography capture wavelength.

FIG. 3 provides an example pattern that is specifically designed to collect light from the confocal array on predetermined pixels in a color detector. Other RGB pixels are used, e.g., to collect white or polychromatic light reflected from the surface of an object being imaged. As shown in FIG. 3, the pixel pattern has repeating quadrants of pixels that are sensitive to different colors. Pixels in color sensor can be fabricated to have a red pixel in the top left and bottom right quadrant. The pixel in the top right quadrant can be green and the pixel in the bottom left quadrant can be blue. These quadrants can be repeated throughout the sensor chip. To provide for simpler and quicker collection of color and topographical data, the bolded red pixels can be coupled with the array of confocal beams such that each confocal beam can be positioned to illuminate each corresponding red pixel in the patterned array of pixels. As shown, the array of confocal beams can be configured in the system such that each beam illuminates every other red pixel in alternating rows (e.g., row 1 and 3) in the sensor pattern. Accordingly, when 3D topographical scan data is acquired, the pixel pattern will collect 3D topographical scan data from the bolded pixels, but not from other pixels on the surface. The remainder of the pixels, as well as the bolded pixels, can be, however, used to collect color image data from the reflected polychromatic (e.g., white) light. As will be generally understood in the art, the RGB sensitive pixels can be processed and used to generate color images of the surface of the object. Similarly, 3D topographical data of the surface can be processed and used, e.g., to generate 3D virtual models of the surface. With the specific pattern and known positions of the pixels, color image data and 3D topographical data of the surface of an object can be combined and overlaid together to be displayed, e.g., to a user.

Figure 4A:
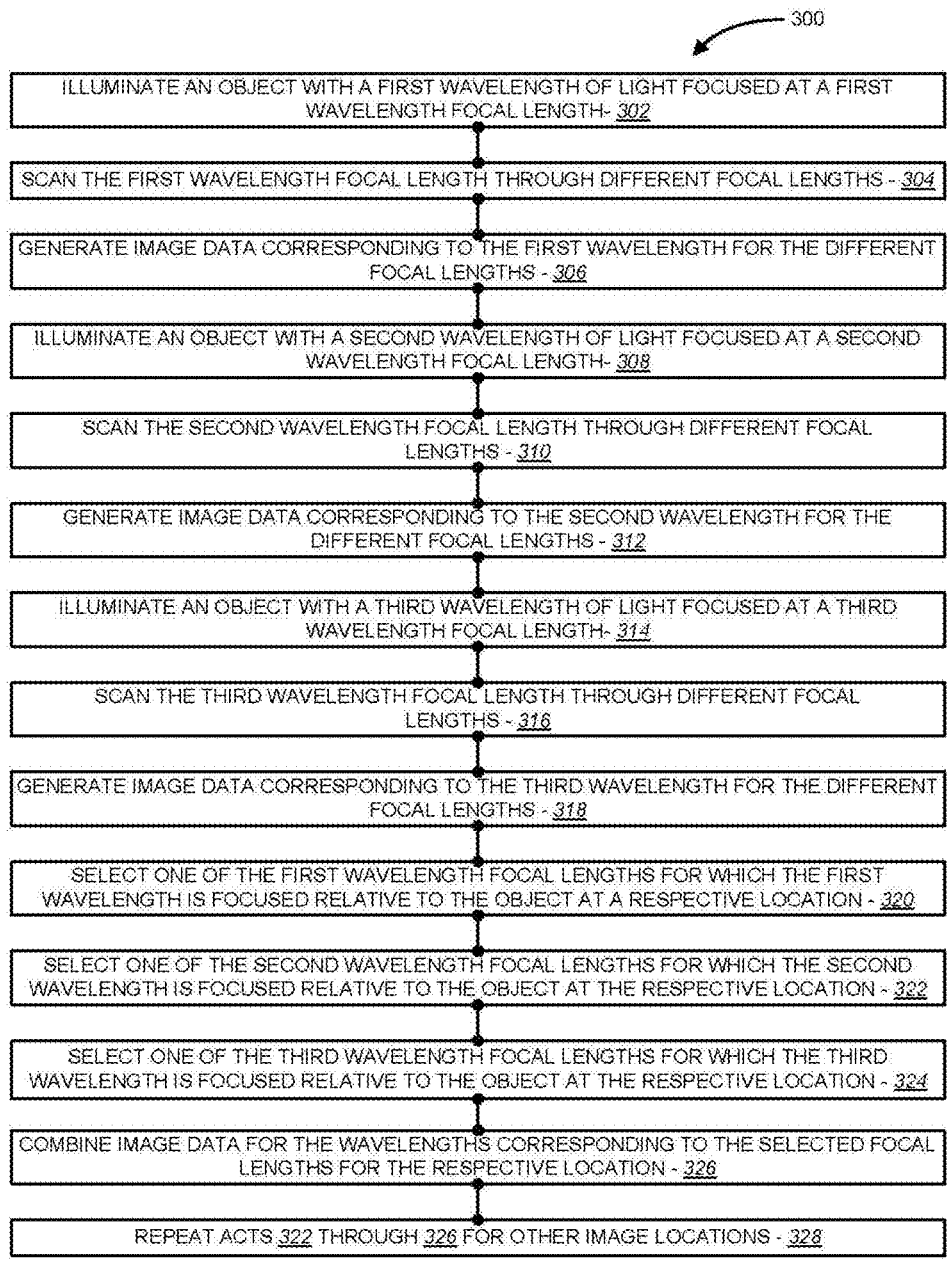
FIG. 4A shows an example method for generating an in-focus color image of an object, in accordance with an embodiment.

In addition to the devices and systems described herein, methods for generating in-focus color images of an object are provided. For example, FIG. 4A illustrates acts of a method 300 for generating an in-focus color image of an object. The method 300 includes act 302 through act 312, act 320, act 322, and act 326. In a preferred embodiment, the method 300 includes optional acts 314 through 318 and optional act 324. Also in a preferred embodiment, acts 322 through act 326 are repeated for a suitable plurality of image locations. Any suitable imaging system, such as any suitable imaging system as described herein can be used to practice the method 300.

In act 302, the object is illuminated with a first wavelength of light that is focused to a first wavelength focal length. For example, a polychromatic light source that produces polychromatic light that includes light having the first wavelength can be used to illuminate the object. A monochromatic light source that produces monochromatic light having the first wavelength can also be used to illuminate the object as an alternative. A suitable optics, such as the optics in the system 200 illustrated in FIG. 2, can be used to focus the first wavelength to a focal length.

In act 304, the first wavelength focal length is scanned through a suitable plurality of different focal lengths. The range of the focal lengths used can be selected to ensure that the imaged portion of the object is enveloped by the range of focal lengths used. The number of focal lengths used can be selected based on a desired accuracy of focus in the resulting focused color image.

In act 306, image data is generated corresponding to the first wavelength of light reflected from the object for the plurality of different first wavelength focal lengths employed. Any suitable image sensor can be used to generate the image data. For example, a color image sensor, such as the detector illustrated in FIG. 3, can be used to generate the image data. In one embodiment, at least one of the red pixels in each repeating quadrant of four pixels is used to generate a signal in response to the first wavelength of light reflected from the object that is incident on the red pixel. In many embodiments, the image data is obtained for each of the different first wavelength focal lengths employed. The image data, however, can be obtained for any suitable set of the first wavelength focal lengths employed. For example, depending on the location in the image, some of the first wavelength focal lengths may be sufficiently out of focus relative to the corresponding location on the object such that generating associated data can be skipped so as to reduce associated data processing. In many embodiments, the image sensor pixels generate signals indicative of the intensity of the reflected light incident thereon. In many embodiments, the image data includes intensity data for the reflected light incident on the detector pixels.

In act 308, the object is illuminated with a second wavelength of light that is focused to a second wavelength focal length. For example, a polychromatic light source that produces polychromatic light that includes light having the second wavelength can be used to illuminate the object. A monochromatic light source that produces monochromatic light having the second wavelength can also be used to illuminate the object as an alternative. A suitable optics, such as the optics in the system 200 illustrated in FIG. 2, can be used to focus the second wavelength to a focal length.

In act 310, the second wavelength focal length is scanned through a suitable plurality of different focal lengths. The range of the focal lengths used can be selected to ensure that the imaged portion of the object is enveloped by the range of focal lengths used. The number of focal lengths used can be selected based on a desired accuracy of focus in the resulting focused color image.

In act 312, image data is generated corresponding to the second wavelength of light reflected from the object for the plurality of different second wavelength focal lengths employed. Any suitable image sensor can be used to generate the image data. For example, a color image sensor, such as the detector illustrated in FIG. 3, can be used to generate the image data. In one embodiment, the green pixel in each repeating quadrant of four pixels is used to generate a signal in response to the second wavelength of light reflected from the object that is incident on the green pixel. In many embodiments, the image data is obtained for each of the different second wavelength focal lengths employed. The image data, however, can be obtained for any suitable set of the second wavelength focal lengths employed. For example, depending on the location in the image, some of the second wavelength focal lengths may be sufficiently out of focus relative to the corresponding location on the object such that generating associated data can be skipped so as to reduce associated data processing. In many embodiments, the image sensor pixels generate signals indicative of the intensity of the reflected light incident thereon. In many embodiments, the image data includes intensity data for the reflected light incident on the detector pixels.

In optional act 314, the object is illuminated with a third wavelength of light that is focused to a third wavelength focal length. For example, a polychromatic light source that produces polychromatic light that includes light having the third wavelength can be used to illuminate the object. A monochromatic light source that produces monochromatic light having the third wavelength can also be used to illuminate the object as an alternative. A suitable optics, such as the optics in the system 200 illustrated in FIG. 2, can be used to focus the third wavelength to a focal length.

In optional act 316, the third wavelength focal length is scanned through a suitable plurality of different focal lengths. The range of the focal lengths used can be selected to ensure that the imaged portion of the object is enveloped by the range of focal lengths used. The number of focal lengths used can be selected based on a desired accuracy of focus in the resulting focused color image.

In optional act 318, image data is generated corresponding to the third wavelength of light reflected from the object for the plurality of different third wavelength focal lengths employed. Any suitable image sensor can be used to generate the image data. For example, a color image sensor, such as the detector illustrated in FIG. 3, can be used to generate the image data. In one embodiment, the blue pixel in each repeating quadrant of four pixels is used to generate a signal in response to the third wavelength of light reflected from the object that is incident on the blue pixel. In many embodiments, the image data is obtained for each of the different third wavelength focal lengths employed. The image data, however, can be obtained for any suitable set of the third wavelength focal lengths employed. For example, depending on the location in the image, some of the third wavelength focal lengths may be sufficiently out of focus relative to the corresponding location on the object such that generating associated data can be skipped so as to reduce associated data processing. In many embodiments, the image sensor pixels generate signals indicative of the intensity of the reflected light incident thereon. In many embodiments, the image data includes intensity data for the reflected light incident on the detector pixels.

In act 320, one of the first wavelength focal lengths for which the first wavelength is focused relative to the object at a respective location is selected. In many embodiments, the selection is based on analysis of the first wavelength reflected from the object at the respective location. For example, the signals generated by a pixel of a detector indicative of intensity of the first wavelength incident thereon can be compared to determine which of the first wavelength focal lengths provides the highest intensity thereby being indicative of the best focus relative to the object for the respective location. In act 322 and act 324, similar selections are made with respect to the second and third wavelength focal lengths.

In act 326, image data for the utilized wavelengths (e.g., first, second, and third wavelengths) corresponding to the selected focal lengths are combined for the respective location. Accordingly, the combined imaged data is generated using in-focus data for each of the utilized wavelengths.

Act 322 through act 326 is repeated for other image locations. Accordingly, the resulting focused color image, at least for an object having a non-trivial, non-planar geometry, will typically be generated using location dependent focal lengths for each of the utilized wavelengths, thereby providing for increased image quality relative to images generated with a single, or non-location dependent focal lengths.

The method 300 can further include additional acts and/or additional details. For example, if a polychromatic light is used or multiple monochromatic light sources are used, the first, second, and third wavelengths can be scanned simultaneously as each type of pixel (e.g. red, green, and blue) in the color image sensor will sense the wavelength of light associated with that pixel. Another alternative is to use a monochrome sensor and use a series of monochrome light sources of different colors and perform a separate scan with each color and use the monochromatic sensor for each color.

Additionally, the first wavelength of light can include a wavelength between about 465 nm and about 485 nm. The second wavelength of light can include a wavelength between about 500 nm and about 520 nm. The third wavelength of light can include a wavelength between about 640 nm and about 660 nm. The first wavelength image data can include intensity and position data for the first wavelength for each of the plurality of first wavelength focal lengths or a suitable subset of the first wavelength focal lengths. The second wavelength image data can include intensity and position data for the second wavelength for each of the plurality of second wavelength focal lengths or a suitable subset of the second wavelength focal lengths. The third wavelength image data can include intensity and position data for the third wavelength for each of the plurality of third wavelength focal lengths or a suitable subset of the third wavelength focal lengths. A white light source can be used to illuminate the object with the first wavelength, the second wavelength, and/or the third wavelength.

The method 300 can also include collecting surface topology data of the object using a scanning system. For example, the scanning system can include a monochromatic light source that is used to illuminate the object with monochromatic light. A focal length of the monochromatic light can be scanned through a plurality of different monochromatic light focal lengths. For each of a plurality of different locations in the focused color image, one of the monochromatic light focal lengths, for which the monochromatic light is focused relative to the object at the respective location, can be selected based on analysis of the monochromatic light reflected from the object at the respective location. The surface topology data can be generated based on the selected monochromatic light focal lengths. The surface topology data and the focused color image of the object can be aligned in a common frame of reference.

The focal length for each respective wavelength being focused relative to the object can be selected so as to result in a reduced blur circle diameter relative to existing approaches. For example, in many embodiments, the focal length for each respective wavelength being focused relative to the object is selected to results in a blur circle diameter not greater than 0.4 mm. In an exemplary embodiment, a blur circle diameter of not greater than 0.4 mm can be achieved by focusing the respective wavelength within 3.2 mm of the object location being imaged. As another example, in more closely focused embodiments, the focal length for each respective wavelength being focused relative to the object is selected to results in a blur circle diameter not greater than 0.2 mm. In an exemplary embodiment, a blur circle diameter of not greater than 0.2 mm can be achieved by focusing the respective wavelength within 1.6 mm of the object location being imaged.

The approaches disclosed herein, including methods like method 300, can be embodied within a suitably configured scanning device. For example, in many embodiments, a scanning device is configured to implement a computer-implemented method for generating a focused color image of an object. The computer-implemented method includes processing image signals corresponding to a first wavelength of light of a plurality of different focal lengths that is reflected from the object so as to generate first wavelength image data. Image signals corresponding to a second wavelength of light of a plurality of different focal lengths that is reflected from the object are processed so as to generate second wavelength image data. The second wavelength is different from the first wavelength. For each of a plurality of different locations in the focused color image, the method includes: (a) selecting one of the first wavelength focal lengths for which the first wavelength is focused relative to the object at the respective location, wherein the selected first wavelength focal lengths for the plurality of different locations in the focused color image comprise at least two different focal lengths; (b) selecting one of the second wavelength focal lengths for which the second wavelength is focused relative to the object at the respective location, wherein the selected second wavelength focal lengths for the plurality of different locations in the focused color image comprise at least two different focal lengths; and (c) combining the first wavelength image data corresponding to the selected first wavelength focal length for the respective location and the second wavelength image data corresponding to the selected second wavelength focal length for the respective location, thereby generating focused color image data for the respective image location for the focused color image of the object.

The methods disclosed herein, such as the method 300, can be practiced via a suitable computer program. For example, in many embodiments, a tangible medium is used to store non-transitory computer readable instructions, that when executed by an imaging system comprising one or more processors, cause the imaging system to perform any suitable method disclosed herein.

Figure 4B:
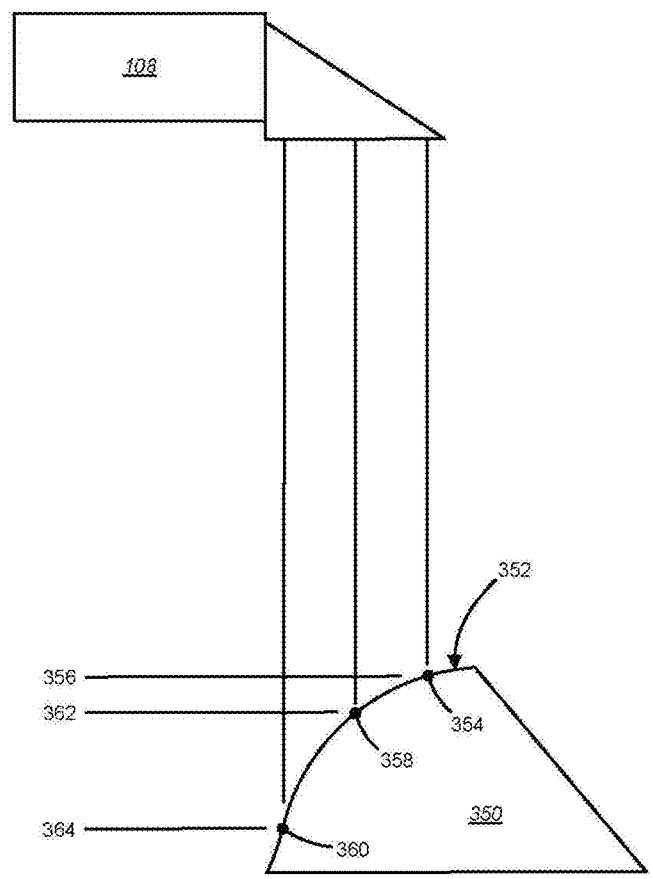
FIG. 4B illustrates how object locations can be out of focus for a particular focal length, in accordance with an embodiments.
Figure 4C:
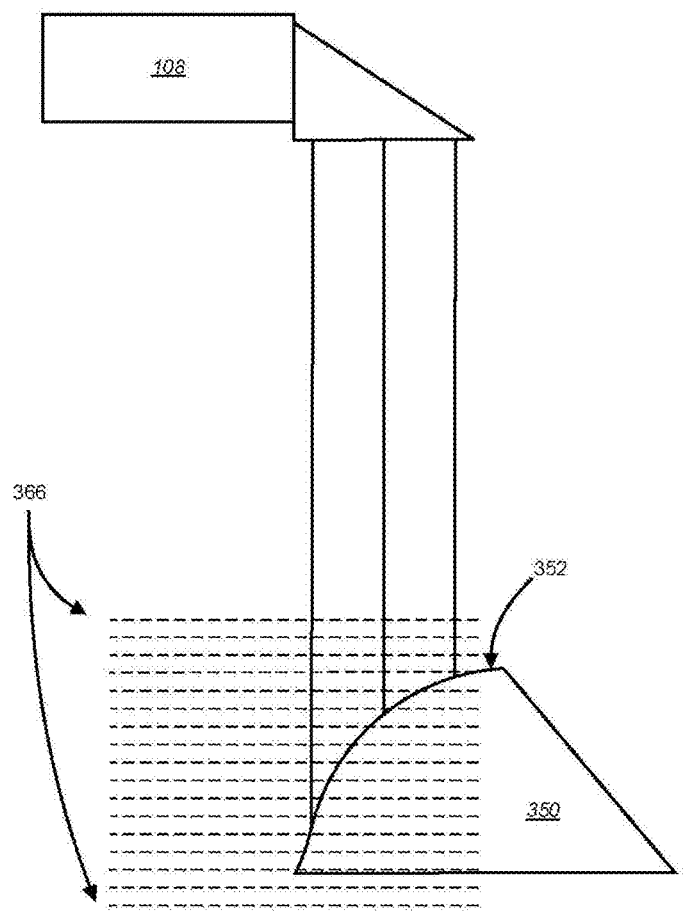
FIG. 4C illustrates a range of focal lengths employed during focal length scanning, in accordance with an embodiments.
Figure 4D:
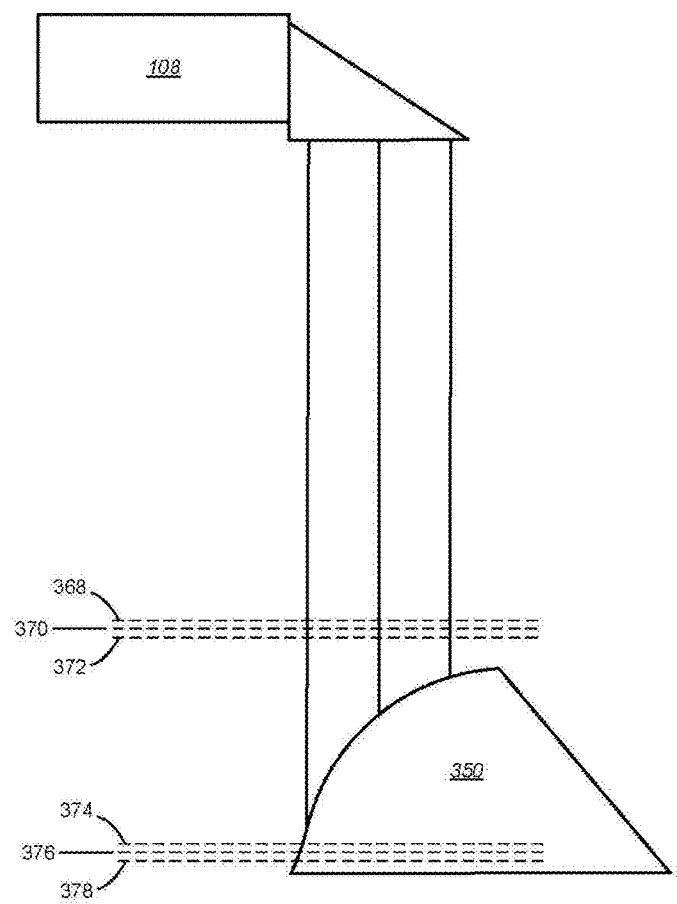
FIG. 4D illustrates focal length differences at time points during focal length scanning that can arise due to chromatic aberration, in accordance with an embodiment.

In accordance with many embodiments, FIGS. 4B through 4D illustrate aspects of generating a focused color image of an object. As illustrated in FIG. 4B, a three-dimensional object 350 includes an external surface 352 that is disposed over a range of distances from a scanner 108 used to generate an image of the object 350. As a result, at least a portion of the external surface 352 will be out of focus for any particular focal length employed by the scanner 108. For example, while a first location 354 on the external surface will be in focus when a first focal length 356 is employed, second and third locations 358, 360 on the external surface 352 will be out of focus. Likewise, the second location 358 will be in focus when a second focal length 362 is employed, but the first and third locations 354, 360 will not be in focus. The third location 360 will be in focus when a third focal length 364 is employed, while the first and second locations 354, 358 will then be out of focus.

In many embodiments, image data for a plurality of focal lengths is obtained for use in generating a focused color image. The plurality of focal lengths is obtained by scanning the focal length of each of the wavelengths (e.g., red, green, and blue) employed. FIG. 4C illustrates a plurality of focal lengths 366, the limits of which extend above and below the external surface 352 of the object 350. Because the image data includes a plurality of focal lengths, a focal length for a respective image location, which corresponds to a respective location on the external surface 352, can be selected so that the respective location on the external surface 352 is in focus. Any suitable approach can be used to select focal lengths for which the respective location on the object is in focus for each of the wavelengths used to construct the in-focus color image. For example, light reflected from the respective object location for a plurality of candidate focal lengths can be analyzed to determine which of the candidate focal lengths corresponds to the best focus of the light relative to the respective object location. In many embodiments, the light reflected from the respective object location is analyzed to identify which of the candidate focal lengths results in maximum intensity of the reflected light. Alternatively, the in-focus situation can be inferred from the high spatial frequency contents of an image portion of the said wavelength. Higher frequency contents indicate better focus proximity. One or more of the wavelengths can be analyzed to determine the distance to the respective object location. The determined distance can then be used for adjacent scan frames where the time between frames is sufficiently small to preclude a significant relative movement between the scanning device and the object being imaged.

In many embodiments, in-focus image data for each object location is generated by combining the in-focus color data for the object location. The in-focus image data for each object location can then be combined to generate an overall in focus color image for the object.

FIG. 4D illustrates chromatic aberration induced variation in focal lengths. When a polychromatic light source is employed, chromatic aberration in the optics can result in the first, second, and third wavelengths having different focal lengths at a given point in time. For example, at a starting point in time during focal length scanning, a corresponding starting blue focal length 368 can be disposed above a corresponding starting green focal length 370, which can be disposed above a corresponding starting red focal length 372. Likewise, at a later point in time of focal length scanning, a corresponding blue focal length 374 is similarly disposed above a corresponding green focal length 376, which is disposed above a corresponding red focal length 378. In many embodiments, such differences between the focal lengths of the wavelengths employed is accounted for when determining which location dependent image data subsets to combine for each of the respective image locations so as to generate the resulting focused color image.

In one aspect, an imaging device or scanner can be positioned near an object (e.g., in a patient's mouth near the patient's teeth). The scanner can be configured to generate both an in-focus color image and 3D topography data. For example, in many embodiments, a scanner employs polychromatic light for color imaging and monochromatic light for 3D topographical imaging. The light for each imaging mode can be focused to a focal length. For example, a blue focal length, a green focal length, and a red focal length can be disposed along a Z-dimension (as shown, e.g., in FIG. 5). A focal length associated with light employed for 3D imaging can also be produced by the scanner. The scanner can scan the focal lengths up and down in the Z-dimension and collect 3D and color image data for the various focal lengths employed. To image a region of an object, the scanner can be held over the region and the focal lengths can be scanned in the Z-dimension over time (e.g., over a time span on the order of milliseconds). During the scanning of the focal lengths, the scanner can be held in a stable position over the object and the focal lengths can be scanned in the Z-dimension. During an up-scanning of the focal lengths, a down-scanning of the focal lengths, or both, color image data and/or 3D topographical data can be collected for the region of the object. After scanning of the focal lengths for the region of the object is complete, the collected color image data and/or 3D topographical data can be processed by a computer system and, e.g., output for visual display. A user holding the device can then move the imaging region to another section of the object (e.g., another section of a patient's teeth) and then acquire additional color and topographical data to then be processed and output to the display. This process can be repeated until an object is completely scanned. The image data from each region of the object can be combined (e.g., using methods for generating a focused color image described herein) to render a full focused color image of the object. For example, a full image of a patient's teeth can be generated to include both 3D topography of the patient's teeth and associated focused color image data of the patient's teeth, gums, or other colored material in the patient's mouth.

As described herein, improved methods and systems are provided for generating color images of an object, including a variety of methods for generating a focused color image of an object. In some embodiments, a first wavelength of light can have a wavelength between about 465 nm and about 485 nm, a second wavelength of light can have a wavelength between about 500 nm and about 520 nm, and a third wavelength of light can have a wavelength between about 640 nm and about 660 nm. Other wavelengths can also be used and configured for a particular application and/or detector being used. For example, a cyan-magenta-yellow (CMY) color scheme can be used, or a red-green-blue (RGB) color scheme can be used.

In many embodiments, white light is used to illuminate the object for which the focused color image is generated, a red-green-blue (RGB) color sensor is used to generate image signals in response to the light reflected from the object, and low dispersed optics are used to deploy the different wavelengths of the white light into different focal planes. And in many presently preferred embodiments, the optical dispersion is designed such that the distance between the red focal plane and the green focal plane is equal to the distance between the green focal plane and the blue focal plane. For example, the optical dispersion can be designed such that when the red wavelength focal plane is located at a reference z-dimension ($Z_0$), the green wavelength focal plane is at the reference z-dimension plus a selected delta-z distance ($Z_0 + \Delta Z$) and the blue wavelength focal plane is at the reference z-dimension plus two times the selected delta-z distance ($Z_0 + 2\Delta Z$). By scanning the focal lengths in a stepwise fashion with each step equal to the selected delta-z distance ($\Delta Z$) between acquisition of color image data, the elemental color data (e.g., red data, green data, and blue data) for three adjacent color image scan frames can be combined to generate in-focus color data for a particular object location. FIGS. 5, 6, 7 and 8 illustrate scanning approaches that can be used in conjunction with an optical system having dispersion that is designed such that the distance between the red focal plane and the green focal plane is equal to the distance between the green focal plane and the blue focal plane. While the scanning approaches illustrated in FIGS. 5, 6, 7, and 8 can be used in conjunction with an optical system having dispersion that is designed such that the distance between the red focal plane and the green focal plane is equal to the distance between the green focal plane and the blue focal plane, any suitable optical system can be used, including optical systems that do not have dispersion that is designed such that the distance between the red focal plane and the green focal plane is equal to the distance between the green focal plane and the blue focal plane. For example, the approaches disclosed herein for generating an in-focus color image can be used in conjunction with an optical system having dispersion such that the distance between the red focal plane and the green focal plane is not equal to the distance between the green focal plane and the blue focal plane. As another example, the approaches disclosed herein for generating an in-focus color image can be used in conjunction with an optical system configured such that the red focal plane, the green focal plane, and/or the blue focal plane are substantially coincident for any particular scan frame.

Figure 5:
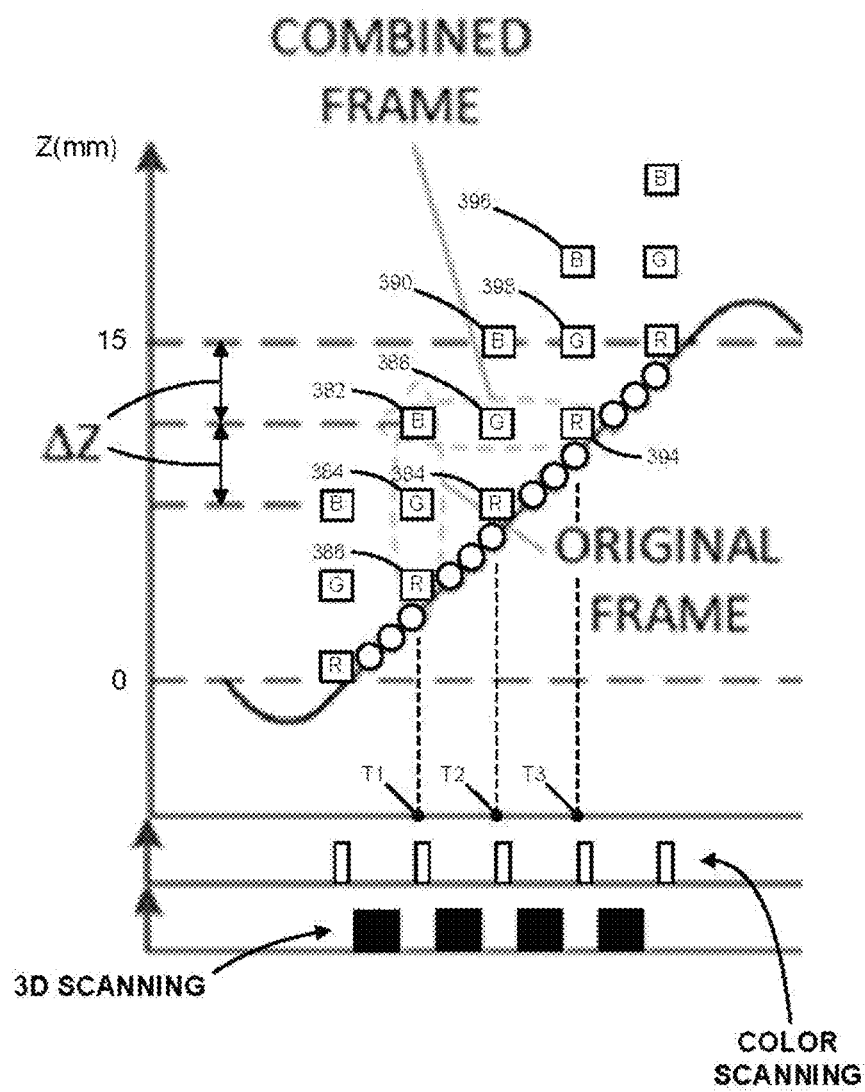
FIGS. 5 through 8 depict example techniques for scanning and generating 3D and/or color image data of an object, in accordance with many embodiments.

FIG. 5 illustrates an approach for obtaining both in-focus color image data and surface topography data during focal length scanning. As shown, focal lengths of the respective wavelengths can be scanned over a distance along a Z-dimension in an interval of time. For example, the focal lengths can be scanned over a range of millimeters or centimeters or more depending on the scale of surface features of an object. FIG. 5 shows scanning over a range of tens to hundreds of millimeters (e.g., as shown, about 10-20 millimeters). The time frame for the scanning can also be on the order of microseconds, milliseconds, or longer. A full scan time for scanning an object can depend, e.g., on the amount of area and/or number of Z-scans used for generating an image. In FIGS. 5 through 8, the time axis is in milliseconds.

In many embodiments, the scanner collects data used for generating a focused color image of the imaged object and/or 3D topographical data representing the imaged object. In the embodiment illustrated in FIG. 5, the scanned object is illuminated with polychromatic light (e.g., white light) at varied time points during scanning of the focal lengths along the Z-direction. In FIG. 5, each time point with white illumination is illustrated with the B, G, and R boxes. The focal lengths for the blue, green, and red light from the white light source can be arranged in different Z-positions, e.g., by tailoring the chromatic aberration of the scanner's optics. The focal lengths of the red, green, and blue light are varied during the scan. Image data can be acquired for each of the focal lengths during the scan. Once in-focus image data is acquired for the respective image locations for each color wavelength employed (e.g., red, green, and blue), the in-focus color data for the respective location can be combined to generate in-focus color data for the respective image location. The in-focus color data for all the respective locations can then be combined to generate an overall in focus color image for the object.

In many embodiments that employ wavelength dependent focal lengths, for example, due to chromatic aberration, the in-focus color image data (e.g., red, green, and blue in-focus image data) that are combined to generate in-focus image data for a particular object location are obtained at different times. For example, referring to FIG. 5, when a particular object location is in focus at a first time point T1 relative to an employed blue wavelength (blue focal position 382), the particular object location is out of focus relative to employed green and red wavelengths (green focal position 384 and red focal position 386). At a second time point T2, the particular object location is in focus relative to the green wavelength employed (green focal position 388) while being out of focus relative to the employed blue and red wavelengths (blue focal position 390 and red focal position 392). At a third time point T3, the particular object location is in focus relative to the red wavelength employed (red focal position 394) while being out of focus relative to the employed blue and green wavelengths (blue focal position 396 and green focal position 398). In such a scenario, the blue image data for the particular object location from the first time point T1 (blue focal position 382) can be combined with the green image data for the particular object location from the second time point T2 (green focal position 388) and the red image data for the particular object location from the third time point T3 (red focal position 394) to generate in-focus color image data for the particular object location. Combination of the image data can, e.g., be carried out using the computer system and processor as described further herein.

In a similar fashion, different object locations with significantly different distance from the scanner will have different in-focus focal lengths. Accordingly, the in-focus color data for such different locations will be obtained at different time points during scanning of the focal lengths.

As shown in FIG. 5, 3D topography data for the object can be obtained during scanning of the focal lengths at time points between the time points at which the in-focus color image data is obtained. For example, between time point I and time point II in FIG. 5, 3D topography data can be obtained by illuminating the object with monochromatic light in the form of an array of separate beams that are each focused to a focal length. In many embodiments, the focal length of the separate monochromatic beams are incrementally scanned through a plurality of different focal lengths and image data for each of the beams is obtained for each focal length. Similar 3D topography can be obtained between time point II and time point III, between time point III and time point IV. The image data for each of the beams can then be analyzed to identify which focal length results in maximum intensity of the reflection of the respective beam from the object surface, thereby being indicative of the location of the best focus of each beam relative to the object surface, which indicates the distance between the scanner and the object surface for the object location from which each beam is reflected.

Figure 6:
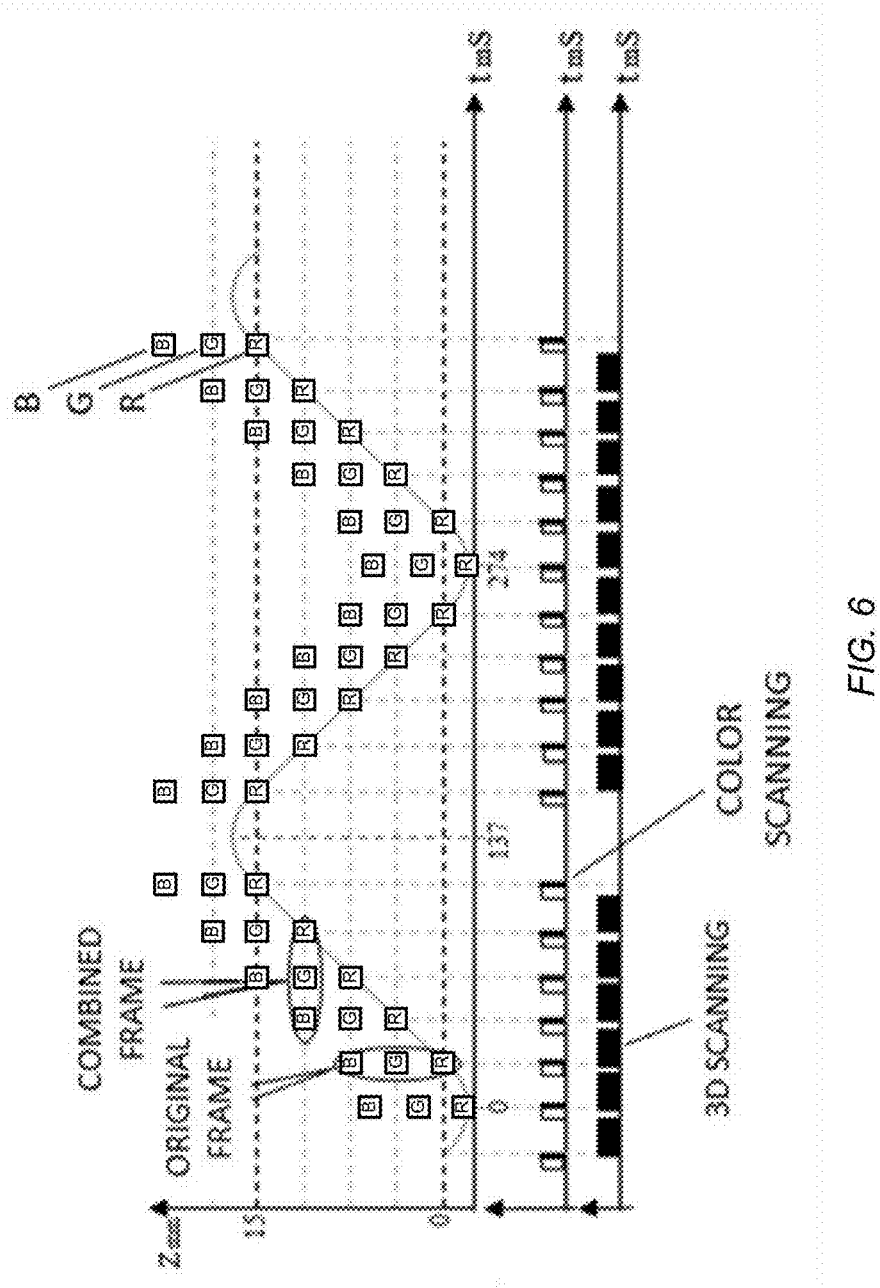
Figure 7:
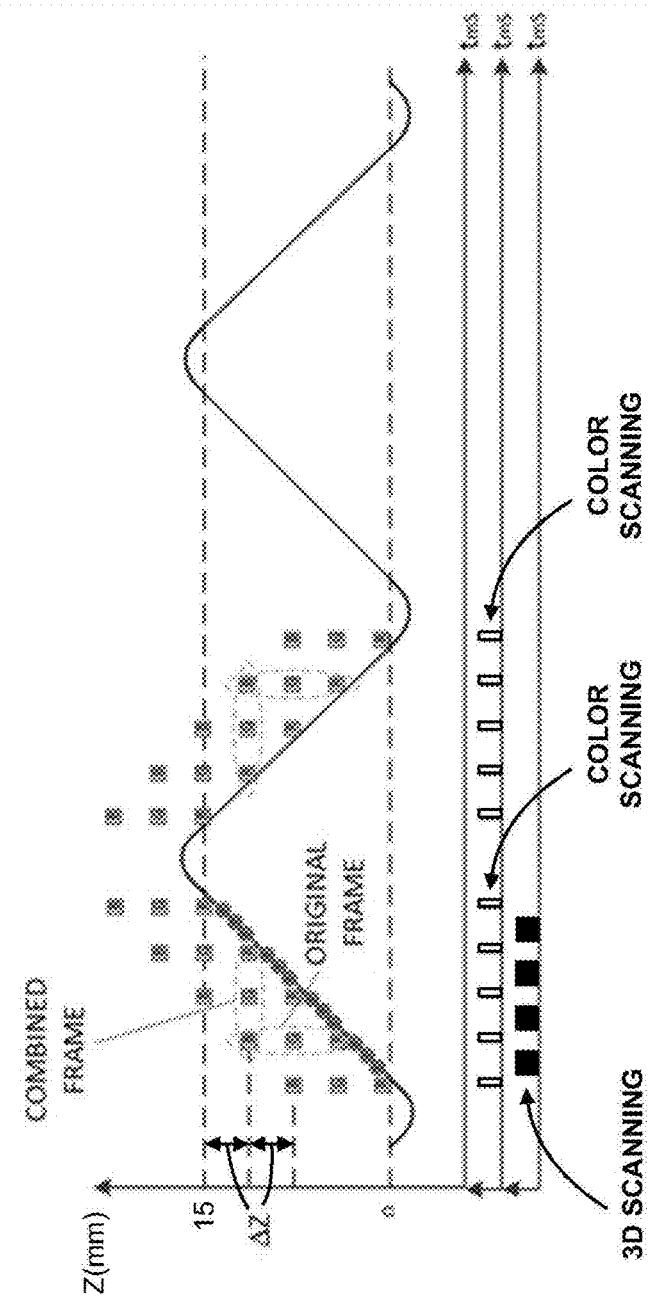

The color image data can be collected at suitable time points during scanning of an object surface. For example, 3D topographical data can be collected through both the up and down scans and either entirely or partially throughout the scans, as well. FIG. 6, for example, shows a combination method of collecting both color 2D image data and 3D topographical data during scanning of an object. As shown, color RGB image data can be generated at time points during focal length scanning along a Z-dimension. In focus color data for a particular object location can be generated, e.g., by combining the color image data from different time points in the scan, in which each color, e.g., RGB, are in focus relative to the particular object location at their respective times. Shown in FIG. 6, the 3D topographical data and the color image data can be collected during both the ups and downs of the focal length scanning procedure. As another example, as shown in FIG. 7, the color image data can be collected on both the up scan and the down scan and the 3D topography data collected only during the up scan.

As described above, the systems can include both imaging optics for 3D confocal imaging as well as 2D color imaging. FIG. 6 depicts an example scanning protocol that can involve staggered collection and/or generation of both color and 3D topographical data of an object. As shown, color image data (e.g., RGB data) can be collected, followed by collection of 3D topographical data of the surface of the object, followed by color image data (e.g., RGB data), and so on. Any combination of collecting color image data and/or 3D topographical data can be employed. For example, 3D topographical data can be collected during suitable time periods and used to generate 3D virtual models of the object, and 2D color image data can be collected during suitable time periods other than those used to collect 3D topographical data. The scanning time used for collecting 3D topographical data can be significantly longer than the time used to collect 2D color image data, for example, 5 times longer, 10 times longer, or 20 or more times longer. Longer multiples, shorter multiples, or any multiples in between can be used.

Figure 8:
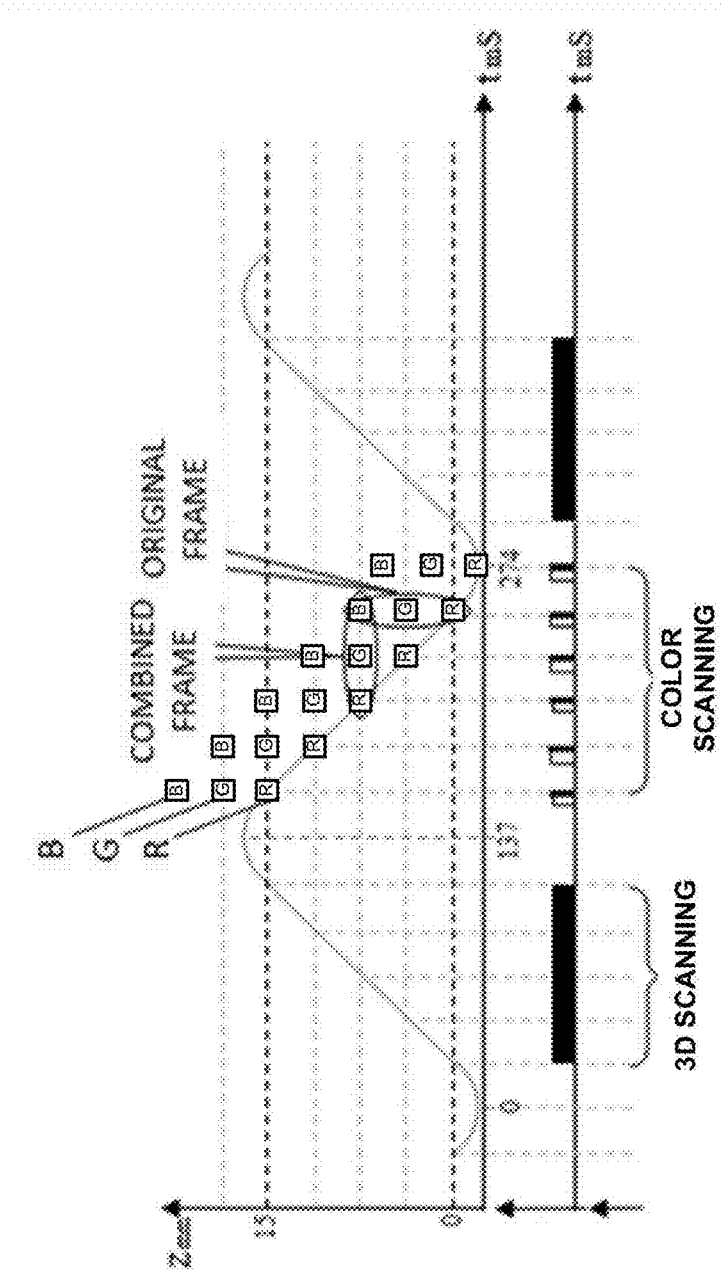

As shown in FIG. 8, the collection of 3D topographical data can be performed during the up scan, and 2D color image data collected during the down scan. As shown, the 2D color image data and the 3D topographical data can be collected independently. It is also envisioned that any of the embodiments described herein, e.g., in FIGS. 5-8, as well as other combinations can be used at anytime during a focal length scanning procedure. For example, some of the ups and downs of the scans during a focal length scanning procedure can include both collection of the 2D color image data and the 3D topographical data. Some of the scans could include collecting the 2D color image data and the 3D topographical data independently.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for generating a focused color image of an object, the system comprising:
   a light source that produces light comprising a first wavelength and light comprising a second wavelength different from the first wavelength;
   an optics system optically coupled to the light source and operable to:
      focus the first wavelength to a first wavelength focal length and scan the first wavelength focal length through a plurality of different first wavelength focal lengths; and
      focus the second wavelength to a second wavelength focal length and scan the second wavelength focal length through a plurality of different second wavelength focal lengths;
   a detector configured to collect first wavelength image data corresponding to the first wavelength of light reflected from the object for the plurality of first wavelength focal lengths and second wavelength image data corresponding to the second wavelength of light reflected from the object for the plurality of second wavelength focal lengths; and
   a processor configured to, for each of a plurality of different locations in the focused color image:
      select one of the first wavelength focal lengths for which the first wavelength is focused relative to the object at the respective location;
      select one of the second wavelength focal lengths for which the second wavelength is focused relative to the object at the respective location; and
      combine the first wavelength image data corresponding to the selected first wavelength focal length for the respective location and the second wavelength image data corresponding to the selected second wavelength focal length for the respective location, thereby generating focused color image data for the respective image location for the focused color image of the object.

2. The system of claim 1, wherein the optics system comprises a movable optical component configured to:
   scan the first wavelength focal length through the plurality of first wavelength focal lengths; and
   scan the second wavelength focal length through the plurality of second wavelength focal lengths.

3. The system of claim 1, wherein:
   the light source produces light comprising a third wavelength different from the first and second wavelengths;
   the optics system is operable to focus the third wavelength to a third wavelength focal length and scan the third wavelength focal length through a plurality of different third wavelength focal lengths;

the detector is configured to collect third wavelength image data corresponding to the third wavelength of light reflected from the object for the plurality of third wavelength focal lengths; and the processor is configured to, for each of the plurality of different locations in the focused color image:

select one of the third wavelength focal lengths for which the third wavelength is focused relative to the object at the respective location; and combine the first wavelength image data corresponding to the selected first wavelength focal length for the respective location, the second wavelength image data corresponding to the selected second wavelength focal length for the respective location, and the third wavelength data corresponding to the selected third wavelength focal length for the respective location; thereby generating the focused color image data for the respective image location for the focused color image of the object.

4. The system of claim 3, wherein at least one of the first wavelength image data, the second wavelength image data, and the third wavelength image data comprises intensity data for the respective wavelength for each of the plurality of the respective at least one wavelength focal lengths.

5. The system of claim 4, wherein:
the first wavelength is a red light wavelength;
the second wavelength is a green light wavelength; and
the third wavelength is a blue light wavelength.

6. The system of claim 4, wherein the respective at least one wavelength image data includes position data corresponding to a plurality of pixels in the detector.

7. The system of claim 1, wherein:
the light source comprises a white light source; and
the detector comprises a color image detector.

8. The system of claim 1, wherein at least one of the selected first wavelength focal lengths and the selected second wavelength focal lengths, for the plurality of different locations in the focused color image, comprise at least two different focal lengths.

9. The system of claim 1, further comprising a scanning system configured to collect surface topology data of the object.

10. The system of claim 9, wherein:
the scanning system comprises a monochromatic light source used to illuminate the object with monochromatic light;
a focal length of the monochromatic light is scanned through a plurality of different monochromatic light focal lengths;
for each of a plurality of different locations in the focused color image, one of the monochromatic light focal lengths is selected, for which the monochromatic light is focused relative to the object at the respective location, based on analysis of the monochromatic light reflected from the object at the respective location; and
the surface topology data is generated based on the selected monochromatic light focal lengths.

11. The system of claim 10, wherein the surface topology data and the focused color image of the object are aligned in a common frame reference.

12. The system of claim 1, wherein the system is wholly or partially incorporated into a hand-held device.

13. The system of claim 1, wherein the light source produces light that simultaneously comprises the first and second wavelengths.

14. The system of claim 1, wherein the selected focal length for each respective wavelength being focused relative to the object results in a blur circle diameter not greater than 0.4 mm.

15. The system of claim 14, wherein the selected focal length for each respective wavelength being focused relative to the object results in a blur circle diameter not greater than 0.2 mm.

16. The system of claim 1, wherein the selection of the first and second wavelength focal lengths is based on at least one of: (a) intensity of light reflected from the object, and (b) spatial frequency contents of an image portion of at least one of the first and second wavelengths reflected from the object.

17. A computer-implemented method for generating a focused color image of an object, the method comprising:

processing image signals corresponding to a first wavelength of light of a plurality of different focal lengths that is reflected from the object so as to generate first wavelength image data;

processing image signals corresponding to a second wavelength of light of a plurality of different focal lengths that is reflected from the object so as to generate second wavelength image data, the second wavelength being different from the first wavelength; and for each of a plurality of different locations in the focused color image:

selecting one of the first wavelength focal lengths for which the first wavelength is focused relative to the object at the respective location;

selecting one of the second wavelength focal lengths for which the second wavelength is focused relative to the object at the respective location; and combining the first wavelength image data corresponding to the selected first wavelength focal length for the respective location and the second wavelength image data corresponding to the selected second wavelength focal length for the respective location, thereby generating focused color image data for the respective image location for the focused color image of the object.

18. The method of claim 17, further comprising:
processing image signals corresponding to a third wavelength of light reflected from the object for a plurality of different focal lengths used to illuminate the object with light that includes the third wavelength so as to generate third wavelength image data, the third wavelength being different from the first wavelength and the second wavelength; and for each of the plurality of different locations in the focused color image:

selecting one of the third wavelength focal lengths for which the third wavelength is focused relative to the object at the respective location; and combining the first wavelength image data corresponding to the selected first wavelength focal length for the respective location, the second wavelength image data corresponding to the selected second wavelength focal length for the respective location, and the third wavelength data corresponding to the selected third wavelength focal length for the respective location; thereby generating the focused color image data for the respective image location for the focused color image of the object.

19. The method of claim 18, wherein the first wavelength of light comprises a wavelength between about 465 nm and about 485 nm, the second wavelength of light comprises a wavelength between about 500 nm and about 520 nm, the third wavelength of light comprises a wavelength between about 640 nm and about 660 nm, or a combination thereof.

20. The method of claim 18, wherein at least one of the first wavelength image data, the second wavelength image data, and the third wavelength image data comprises intensity data for the respective wavelength for each of the plurality of the respective at least one wavelength focal lengths.

21. The method of claim 17, wherein the image signals are generated in response to reflections from the object produced via white light illumination of the object.

22. The method of claim 17, further comprising processing image signals to generate surface topology data of the object.

23. The method of claim 22, wherein the imaging signals processed to generate the surface topology data are generated in response to reflections from the object of monochromatic light that is scanned through a plurality of different focal lengths, the method further comprising:
   for each of a plurality of different locations in the focused color image, selecting one of the monochromatic light focal lengths, for which the monochromatic light is focused relative to the object at the respective location, based on analysis of the monochromatic light reflected from the object at the respective location; and
   generating the surface topology data based on the selected monochromatic light focal lengths.

24. The method of claim 23, wherein the surface topology data and the focused color image of the object are aligned in a common frame of reference.

25. The method of claim 17, wherein the selected focal length for each respective wavelength being focused relative to the object results in a blur circle diameter not greater than 0.4 mm.

26. The method of claim 25, wherein the selected focal length for each respective wavelength being focused relative to the object results in a blur circle diameter not greater than 0.2 mm.

27. The method of claim 17, wherein the selection of the first and second wavelength focal lengths is based on at least one of: (a) intensity of light reflected from the object, and (b) spatial frequency contents of an image portion of at least one of the first and second wavelengths reflected from the object.

28. A system for generating a focused color image of an object in low-light conditions, the system comprising: a color detector comprising a two-dimensional pixel array that includes: (a) a plurality of red pixels distributed within the pixel array, (b) a plurality of green pixels distributed within the pixel array, and (c) a plurality of blue pixels distributed within the pixel array; wherein each of the red pixels is configured to detect a red wavelength of light reflected from the object, each of the green pixels is configured to detect a green wavelength of light reflected from the object, and each of the blue pixels is configured to detect a blue wavelength of light reflected from the object, and wherein the number of red pixels is greater than the number of green pixels, and the number of red pixels is greater than the number of blue pixels;
   and a processor configured to process signals received from the red pixels, the green pixels, and the blue pixels to: generate red wavelength image data corresponding to the red wavelength of light reflected from the object for a plurality of red wavelength focal lengths;
   generate green wavelength image data corresponding to the green wavelength of light reflected from the object for a plurality of green wavelength focal lengths;
   generate blue wavelength image data corresponding to the blue wavelength of light reflected from the object for a plurality of blue wavelength focal lengths;
   for each of a plurality of different locations in the focused color image: select one of the red wavelength focal lengths for which the red wavelength is relative to the object at the respective location, wherein the selected red wavelength focal lengths for the plurality of different locations in the focused color image comprise at least two different focal lengths;
   select one of the green wavelength focal lengths for which the green wavelength is focused relative to the object at the respective location, wherein the selected green wavelength focal lengths for the plurality of different locations in the focused color image comprise at least two different focal lengths;
   select one of the blue wavelength focal lengths for which the blue wavelength is focused relative to the object at the respective location, wherein the selected blue wavelength focal lengths for the plurality of different locations in the focused color image comprise at least two different focal lengths;
   and combining the red wavelength image data corresponding to the selected red wavelength focal length for the respective location, the green wavelength image data corresponding to the selected green wavelength focal length for the respective location, and the blue wavelength data corresponding to the selected blue wavelength focal length for the respective location, thereby generating the focused color image data for the respective image location for the focused color image of the object.

29. The system of claim 28, wherein the processor is configured to process signals from the color detector to generate surface topology data for the object, the system further comprising an optics system, the optics system and the color detector being configured to couple an array of confocal beams used to generate the surface topology for the object with an array of the red pixels such that each confocal beam illuminates a corresponding red pixel in the array of red pixels.

30. The system of claim 28, wherein the selected focal length for each respective wavelength being focused relative to the object results in a blur circle diameter not greater than 0.4 mm.

31. The system of claim 30, wherein the selected focal length for each respective wavelength being focused relative to the object results in a blur circle diameter not greater than 0.2 mm.

32. The system of claim 28, wherein the selection of the red, green, and blue wavelength focal lengths is based on at least one of: (a) intensity of light reflected from the object, and (b) spatial frequency contents of an image portion of at least one of the red, green, or blue wavelengths reflected from the object.

33. The system of claim 28, wherein the system is configured to image an oral cavity of a patient.

* * * * *